United States Patent [19]

Wilk et al.

[11] Patent Number: 5,250,074
[45] Date of Patent: * Oct. 5, 1993

[54] SURGICAL INSTRUMENT ASSEMBLY AND ASSOCIATED TECHNIQUE

[76] Inventors: Peter J. Wilk, 185 West End Ave., New York, N.Y. 10023; Jonathan Tiefenbrun, 62 Country Rd., Mamaroneck, N.Y. 10543

[*] Notice: The portion of the term of this patent subsequent to Aug. 17, 2010 has been disclaimed.

[21] Appl. No.: 914,160

[22] Filed: Jul. 14, 1992

[51] Int. Cl.5 .................................. A61B 17/28
[52] U.S. Cl. ............................. 606/207; 606/158
[58] Field of Search ............... 606/205-211, 606/119, 120, 127, 128, 157, 158, 191, 198, 201-203, 121, 122, 124; 81/83, 483; 294/99.2

[56] References Cited

U.S. PATENT DOCUMENTS

| | | | |
|---|---|---|---|
| 2,549,731 | 4/1951 | Wattley | 606/206 |
| 2,637,320 | 5/1953 | Greenberg | 606/127 |
| 3,503,397 | 3/1970 | Fogarty et al. | 606/207 |
| 3,675,656 | 7/1972 | Hakim | 606/202 |
| 4,586,501 | 5/1986 | Calarcq | 606/158 |
| 4,708,140 | 11/1987 | Baron | 606/201 |

*Primary Examiner*—John D. Yasko
*Assistant Examiner*—William Lewis
*Attorney, Agent, or Firm*—R. Neil Sudol; Henry D. Coleman

[57] ABSTRACT

A surgical instrument assembly comprises an elongate member provided at a distal end with a clamping member having a pair of opposed jaws. Each of the jaws includes an elongate substantially linear arm. The instrument assembly additionally comprises an actuator mehanism mounted to the elongate member and operatively connected to the jaws for alternately opening and closing the jaws, as well as at least one balloon element attached to the jaws so as to form a cushion upon inflation of the balloon element. An inflation device is operatively connected to the balloon element for inflating the balloon from a collapsed insertion configuration to an expanded use configuration.

16 Claims, 3 Drawing Sheets

SURGICAL INSTRUMENT ASSEMBLY AND ASSOCIATED TECHNIQUE

BACKGROUND OF THE INVENTION

This invention relates to a surgical instrument assembly and an associated surgical technique.

During the performance of laparoscopic operations, it is frequently necessary to move an organ such as an intestine or an artery in order to reach an underlying organ. Such large tubular organs cannot be easily manipulated in laparoscopic surgery. Existing instruments such as grasping forceps have operating tips (e.g., jaws) which are basically too small to grasp a colon or major artery and move the organ without injury thereto.

Existing laparoscopic instruments are also ineffective to clamp large organs such as an intestine or an artery. Such a clamping operation would be helpful in trauma cases, for example, to prevent spillage of fecal matter from a perforated intestine.

OBJECTS OF THE INVENTION

An object of the present invention is to provide a surgical instrument or instrument assembly which may be used to grasp and partially shift larger internal organs of a patient such as the colon or the aorta.

Another, related object of the present invention is to provide such a surgical instrument or instrument assembly which may be used in laparoscopic surgery to grasp and partially shift larger internal organs of a patient such as the colon or the aorta.

An associated object of the present invention is to provide a surgical technique which may be used to grasp and partially shift larger internal organs of a patient such as the colon or the aorta, particularly in laparoscopic surgery but not exclusively limited thereto.

Yet another object of the present invention is to provide a surgical technique and an associated instrument assembly which may be used to clamp larger internal organs of a patient such as the colon or the aorta, particularly in laparoscopic surgery but not exclusively limited thereto.

These and other objects of the present inventions will be apparent from the following descriptions and the drawings.

SUMMARY OF THE INVENTION

A surgical instrument assembly comprises, in accordance with the present invention, an elongate member provided at a distal end with a clamping member which has a pair of opposed jaws each including an elongate substantially linear clamping arm extending parallel to a longitudinal axis of the elongate member. The instrument assembly further comprises an actuator mounted to the elongate member and operatively connected to the jaws for alternately opening and closing the jaws so that the arms of the jaws move alternately away and towards one another in a direction perpendicular to the axis.

Pursuant to another feature of the present invention, the instrument assembly also comprises at least one balloon element attached to the jaws so as to form a cushion upon inflation of the balloon element and an inflation mechanism or device operatively connected to the balloon element for inflating the balloon from a collapsed insertion configuration to an expanded use configuration.

According to another feature of the present invention, a rotation device is mounted to the elongate member for pivoting the clamping member about an axis extending orthogonally with respect to the elongate member.

Preferably, the arms of the jaws extend parallel to one another. During insertion of the distal end of the instrument assembly into a patient, for example, through a trocar sleeve in a laparoscopic operation, the arms also extend parallel to a longitudinal axis of the elongate member.

Pursuant to a feature of the present invention, the actuator mechanism includes a screw mechanism. Alternatively, the actuator mechanism includes a rack and pinion type mechanism.

According to a further feature of the present invention, the balloon element is one of a pair of balloon elements each attached to a respective one of the jaws.

Pursuant to a specific feature of the present invention, the inflation device includes an auxiliary balloon attached to the elongate member at a proximal end thereof. The auxiliary balloon may be provided with a locking mechanism for temporarily preventing a flow of pressurization fluid towards or away from the balloon elements on the jaws.

The arms are preferably rigid elements.

A surgical method comprises, in accordance with the present invention, the steps of (a) inserting a distal end of an elongate member into a patient's abdomen, and (b) upon the step of inserting, opening a clamping member connected to the elongate member at a distal end thereof, thereby forming a pair of jaws, the step of opening including the step of separating a pair of parallel arms by shifting the arms perpendicularly away from one another. The method further comprises the steps of (c) moving the jaws towards an internal organ of the patient to insert a portion of the organ between the jaws, and (d) shifting the arms towards one another to at least partially close the jaws about the organ. The shifting may be implemented by operating a screw mechanism mounted to the elongate member.

Pursuant to another feature of the present invention, the method comprises the additional step of inflating a balloon element connected to the jaws, thereby forming a cushion for clamping the organ. Preferably, the balloon element(s) is in a collapsed configuration during the step of inserting.

Where the balloon element is one of a pair of balloon elements attached to respective ones of the jaws, the step of inflating comprises the step of inflating the balloon elements simultaneously.

The inflation of the balloon element or elements may be executed prior to or after the positioning of the jaws about an organ to be grasped and moved.

Accordingly, a large internal organ such as a colonic section or a portion of the aorta may be grasped and clamped in a method in accordance with the present invention. In the event of a traumatized or perforated organ such as the colon, the organ may be temporarily clamped on opposite sides of the perforation to prevent the spilling of fecal material into the abdomen, possibly infecting other organs. The perforation may then be repaired or patched.

In an optional step in accordance with the present invention, the organ is displaced relative to other organic tissues of the patient by exerting a force on the tubular member and the jaws. This displacement enables a surgeon to reach underlying tissues which would otherwise be difficult to access.

An instrument assembly and surgical method in accordance with the present invention is especially adapted to use in a laparoscopic procedure. In that event, the distal end of the instrument assembly is inserted into the patient's abdomen through a trocar sleeve or laparoscopic cannula which is disposed in and traverses the abdominal wall of the patient.

A surgical instrument or instrument assembly in accordance with the present invention may be used to grasp and partially shift larger internal organs of a patient such as the colon or the aorta. The parallel configuration of the grasping arms or jaws facilitates insertion of organs between the jaws and is especially useful in clamping the hepatic triad during, for example, trauma surgery or a cholecestectomy, and in clamping arteries. Where an organ such as the colon is perforated, a pair of instrument assemblies in accordance with the invention may be used to temporarily clamp the colon on opposite sides of the perforation prior to a surgical closure of the perforation.

A surgical instrument or instrument assembly in accordance with the present invention may be used to grasp and partially shift larger internal organs of a patient such as the colon or the aorta. The balloon elements serve to spread the area over which the grasping and clamping forces are exerted, thereby reducing the force at any one location. The balloon elements thereby function to cushion the jaws.

DETAILED DESCRIPTION

Figure 1:
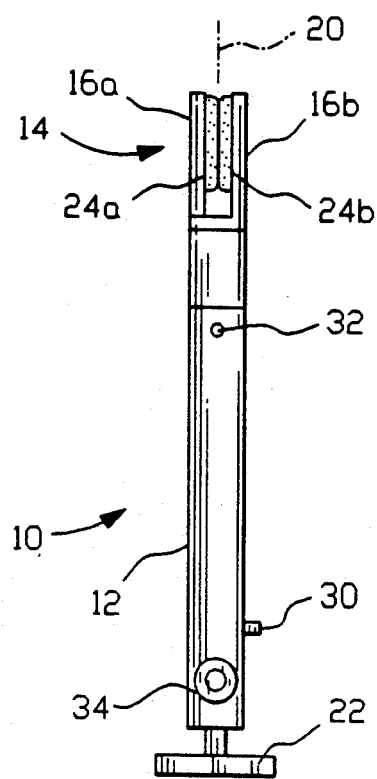
FIG. 1 is a schematic side elevation view of a laparoscopic type surgical clamp in accordance with the present invention, showing a pair of jaws in a closed configuration.

As illustrated in FIG. 1, a laparoscopic type surgical instrument clamp 10 comprises an elongate tubular member 12 provided at a distal end with a clamping member 14. Clamping member 14 has a pair of opposed jaws 16a and 16b each including an elongate substantially linear clamping arm extending parallel to a longitudinal axis 20 of elongate tubular member 12. An actuator 22 is mounted to elongate tubular member 12 and is operatively connected to jaws 16a and 16b for alternately opening and closing the jaws 16a and 16b so that the arms move alternately away and towards one another in a direction perpendicular to axis 20.

Instrument assembly 10 also comprises a pair of balloons or bladders 24a and 24b attached to jaws 16a and 16b along inwardly facing sides thereof so as to cushion the jaws with respect to an organ which is being clamped. As illustrated in general in FIG. 3, balloons 24a and 24b communicate with a source 26 of pressurized gas (e.g., CO2) or saline solution via a valve mechanism 28 and a port 30 at the proximal end of tubular member 12.

Figure 2:
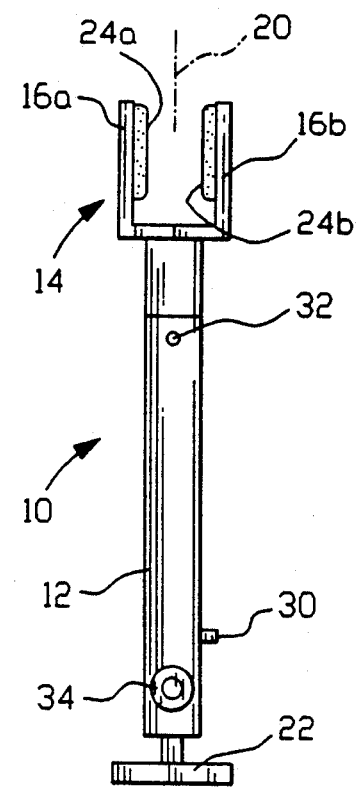
FIG. 2 is a side elevational view similar to FIG. 1, showing the jaws in an opened configuration.
Figure 3:
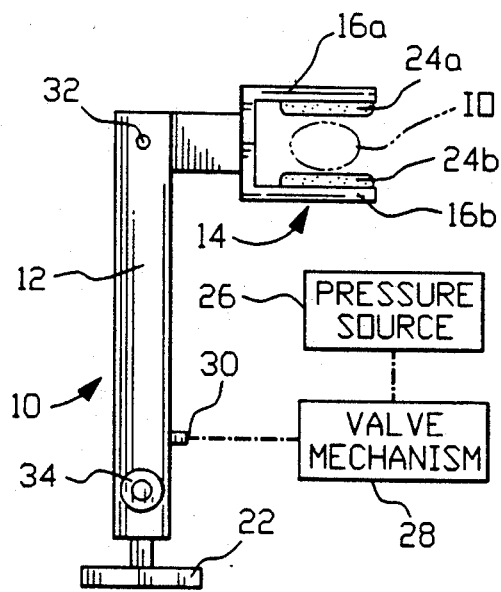
FIG. 3 is a side elevational view similar to FIGS. 1 and 2, showing the jaws in an opened configuration rotated 90° with respect to the axis or shaft of the instrument.

As illustrated in FIG. 1, balloons 24a and 24b are in a collapsed or deflated configuration when jaws 16a and 16b are inserted into a patient at the onset of a laparoscopic surgical procedure. FIG. 2 shows balloons 24a and 24b remaining in the collapsed configuration upon an opening of jaws 16a and 16b by a rotation of actuator knob 22. In FIG. 3, balloons 24a and 24b are still in the collapsed configuration upon a manipulation of instrument assembly 10 so that a tubular internal organ 10 is disposed between opened jaws 16a and 16b.

Figure 8:
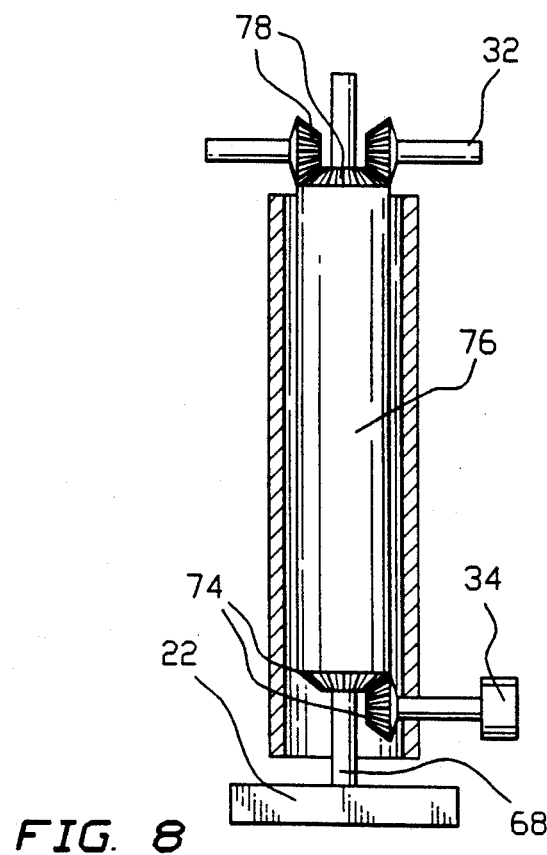
FIG. 8 is a partial schematic longitudinal cross-sectional view of a laparoscopic type clamp in accordance with the present invention, showing a drive mechanism for a rotating joint of the clamp.
Figure 5A:
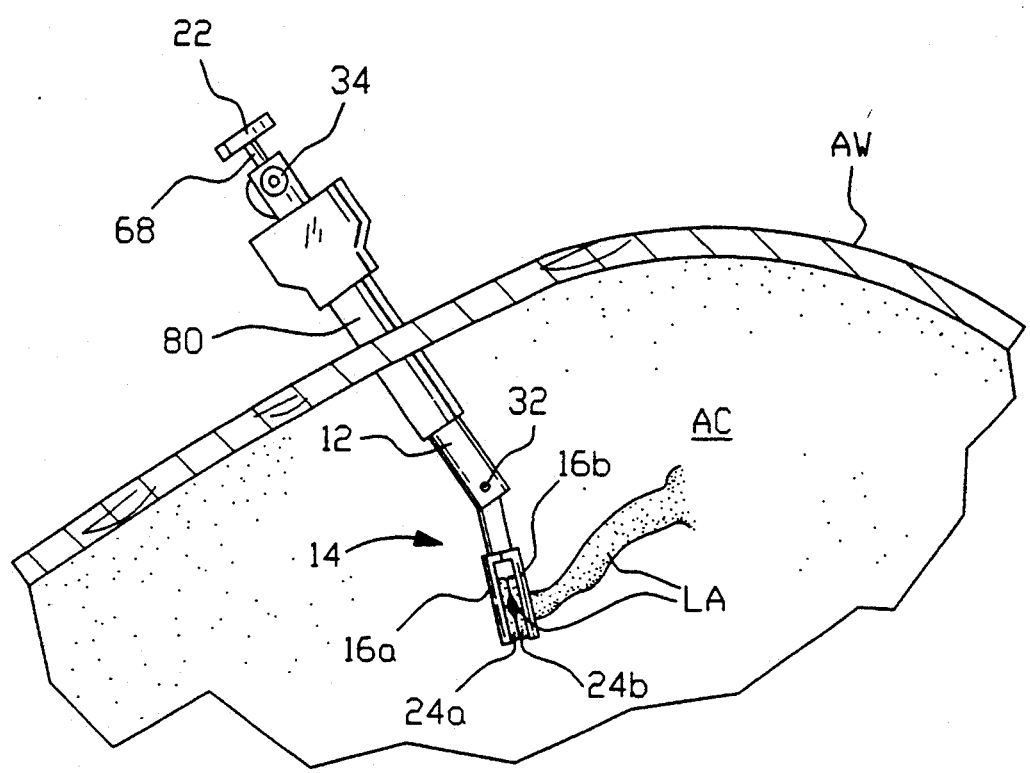

Clamping member 14 is pivotably attached to the distal end of tubular member 12 for limited rotation about a pivot pin 32 extending perpendicularly to longitudinal instrument axis 20. A rotary actuator knob 34 is mounted to tubular member 12 at the proximal end thereof for enabling controlled rotation of clamping member 14 about pin 32 upon insertion of the distal end of instrument assembly into a patient's abdominal cavity through a laparoscopic trocar sleeve (see FIG. 8).

Generally, the actuator mechanism for alternately opening and closing jaws 16a and 16b is separate and independent of the actuator mechanism for rotating clamping member 14 about pin 32. Accordingly, jaws 16a and 16b may be opened prior to (FIG. 2) or subsequently to a pivoting of clamping member 14 about pin 32. The actuator mechanism for alternately opening and closing jaws 16a and 16b may incorporate a rack and pinion arrangement as described in detail hereinafter with reference to FIG. 7. Alternatively, that actuator mechanism may take other forms equivalent to those described and illustrated herein, such as a hydraulic circuit moving the jaws in opposition to a biasing spring force or a spring loaded camming mechanism.

It is to be noted that the grapsing or clamping arms of jaws 16a and 16b extend parallel to one another, thereby facilitating positioning of jaws 16a and 16b about an internal organ of a patient during laparoscopic surgery or other procedure.

Figure 4:
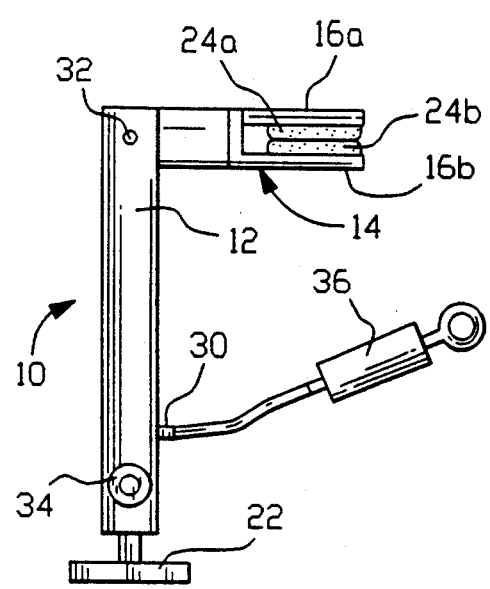
FIG. 4 is a side elevational view, similar to FIG. 3, showing the jaws in a closed configuration and a rotated position.

FIG. 4 illustrates a specific form of pressure source 26, namely, a hypodermic type syringe 36 connected to balloons 24a and 24b via port 30. Syringe 36 is initially filled with a saline solution. A locking element may be provided on syringe 36 to temporarily hold the pressurizing fluid in balloons 24a and 24b upon inflation thereof.

Figure 5:
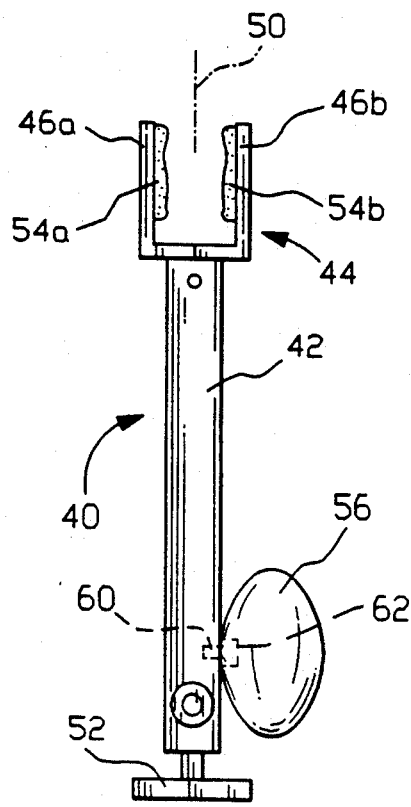
FIG. 5 is a schematic side elevational view of a modified laparoscopic type surgical clamp, showing jaws in an opened configuration and balloons on the jaws in a deflated or collapsed configuration.
Figure 6:
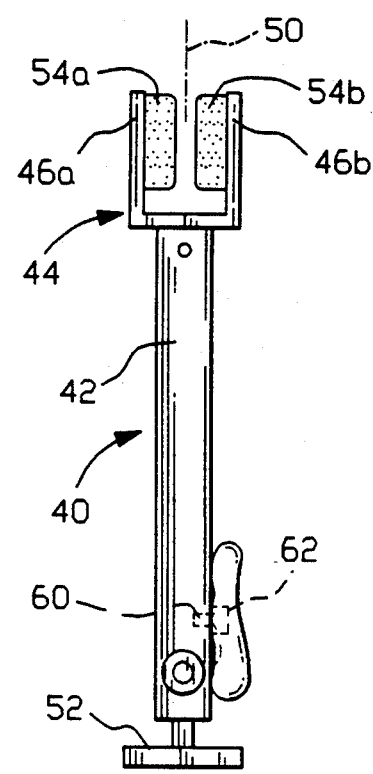
FIG. 6 is a side elevational view similar to FIG. 5, showing the jaws opened and the balloons in an inflated or expanded configuration.

As depicted in FIGS. 5 and 6, a modified laparoscopic type surgical instrument clamp 40 comprises an elongate tubular member 42 provided at a distal end with a clamping member 44. Clamping member 44 has a pair of opposed jaws 46a and 46b each including an elongate substantially linear clamping arms extending parallel to a longitudinal axis 50 of elongate tubular member 42. An actuator 52 is mounted to elongate tubular member 42 and is operatively connected to jaws 46a and 46b for alternately opening and closing the jaws 46a and 46b so that the clamping or grasping arms move alternately away and towards one another in a direction perpendicular to axis 50.

Instrument assembly 40 additionally comprises a pair of balloons or bladders 54a and 54b attached to jaws 46a and 46b along inwardly facing sides thereof so as cushion the jaws with respect to an organ which is being clamped. Balloons 54a and 54b communicate with a source 56 of pressurized gas (e.g., $CO_2$) or saline solution in the form of an auxiliary bladder or balloon connected to a port 60 at the proximal end of tubular member 42 via a manually operated valve element 62 such as a clip.

FIG. 5 illustrates balloons 44a and 44b in a collapsed configuration, bladder 56 being in an expanded state. Upon a manual crushing of bladder 56 which forces fluid under pressure from bladder 56 towards balloons 44a and 44b, balloons 44a and 44b expand, as illustrated in FIG. 6. Clip 62 may be manually worked to close communication between balloons 44a and 44b annd bladder 56, thereby locking the balloons in the expanded configuration.

Figure 7:
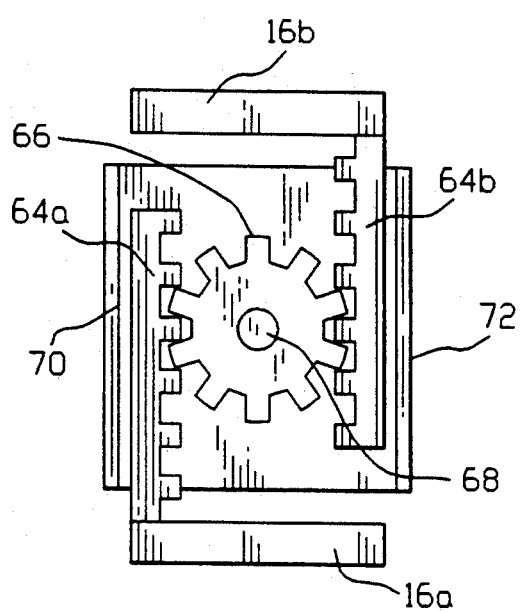
FIG. 7 is a schematic transverse cross-sectional view of a portion of a laparoscopic type clamp in accordance with the present invention, showing a drive mechanism for jaws of the clamp.

As illustrated in FIG. 7, a mechanism for opening and closing jaws 16a and 16b (or jaws 46a and 46b) comprises a pair of toothed rack members 64a and 64b rigid with respective jaws 16a and 16b and extending perpendicularly with respect to longitudinal axis 20. Rack members 64a and 64b intermesh with a toothed gear or pinion 66 attached to a distal end of a shaft 68 which extends longitudinally through tubular member 12, generally coaxially with respect to axis 20. Upon a rotation of shaft 68 about axis 20 in response to a manual turning of actuator knob 22, pinion 66 rotates and shifts rack members 64a and 64b, and accordingly jaws 16a and 16b, towards or away from one another. Alignment elements 70 and 72 are provided on tubular member 12 for maintaining rack members 64a and 64b and jaws 16a and 16b in their respective orientations during use of the instrument assembly.

As depicted in FIG. 3, a rotator assembly for pivoting clamping member 14 about pin 32 comprises a first pair of beveled gears 74 connected on an input side to actuator knob 34 and on an output side to an inner tubular member 76 coaxial with tubular member 12 and connected at a distal end to two or three beveled gears 78 which are connected to clamping member 14 at pivot pin 32. Shaft 68 traverses inner tubular member 76.

As depicted in FIG. 9, a distal end of tubular member 12 or 42 is inserted into a patient's abdominal cavity AC through a trocar sleeve 80 which has been positioned in the abdominal wall AW. During this insertion step, jaws 16a and 16b (or 46a, 46b) are in a closed configuration (FIG. 1). Upon insertion of tubular member 12 or 42 so that the distal end thereof protrudes into the abdominal cavity AC, actuator knob 22 is turned to spread jaws 16a and 16b apart from one another (FIG. 2). Instrument assembly 10 or 40 is then manipulated to move jaws 16a and 16b (or 46a, 46b) towards an internal organ such as a large artery LA to insert a portion of the organ between the jaws. If necessary, knob 34 is turned to pivot clamping member 14 about pin 32 (FIGS. 3 and 9). Prior to or after the manipulation of the instrument assembly to dispose organ LA between jaws 16a and 16b, balloons 24a and 24b are inflated to provide a cushioning function.

If necessary, actuator knob 22 is turned to close jaws 16a and 16b upon organ LA, thereby firmly grasping the organ and blocking fluid flow therethrough. Organ LA may then be displaced relative to other organic tissues of the patient by exerting a force on jaws 16a and 16b via tubular member 12.

After the laparoscopic procedure utilizing the instrument assembly, jaws 16a and 16b are opened and balloons 24a and 24b deflated. The instrument assembly may then be retracted away from the organ LA. Jaws 16a and 16b must then be closed, in order to enable the user to withdraw the instrument through trocar sleeve 80.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for example, that surgical instrument assemblies in accordance with the present invention may be utilized in operations other than laparoscopic surgery. Even in open abdominal surgery, it is frequently necessary to move an organ such as an intestine or an artery in order to reach an underlying organ.

It is to be additionally noted that in some cases, depending on the size of the organ to be grasped and purpose of the manuever, the inflation of the balloon elements on the jaws of the instrument may provide a sufficient clamping force so that the jaws need not be closed.

Balloon elements in accordance with the present invention may take any of a number of equivalent forms. For example, a single balloon (not illustrated) with a generally U-shaped form may be attached to prongs or jaws of an instrument assembly in accordance with the present invention. Additionally, or alternatively, the balloons may substantially surround the prongs or jaws rather than being disposed only along the inner surfaces thereof.

Accordingly, it is to be understood that the drawings and descriptions herein are profferred by way of example to facilitate comprehension of the invention and should not be construed to limit the scope thereof.

What is claimed is:

1. A surgical instrument assembly comprising:
   an elongate member provided at a distal end with a clamping member having a pair of opposed jaws each including an elongate substantially linear clamping arm extending parallel to a longitudinal axis of said elongate member; and
   actuator means mounted to said elongate member and operatively connected to said jaws for alternately opening and closing said jaws so that the arms of said jaws move alternately away and towards one another in a direction perpendicular to said axis.

2. The instrument assembly defined in claim 1, further comprising:
   at least one balloon element attached to said jaws so as to form a cushion upon inflation of the balloon element; and
   inflation means operatively connected to said balloon element for inflating same from a collapsed insertion configuration to an expanded use configuration.

3. The instrument assembly defined in claim 1, further comprising rotation means mounted to said elongate member for pivoting said clamping member about an axis extending orthogonally with respect to said longitudinal axis.

4. The instrument assembly defined in claim 1 wherein said actuator means includes a rack and pinion type mechanism.

5. The instrument assembly defined in claim 1 wherein said balloon element is one of a pair of balloon elements each attached to a respective one of said jaws.

6. The instrument assembly defined in claim 1 wherein said inflation means includes an auxiliary balloon attached to said elongate member at a proximal end thereof.

7. The instrument assembly defined in claim 1 wherein said arms are rigid elements.

8. The instrument assembly defined in claim 1, further comprising a trocar sleeve, said elongate member traversing said trocar sleeve.

9. A surgical method comprising the steps of:
inserting a distal end of an elongate member into a patient's abdomen;
upon said step of inserting, opening a clamping member connected to said elongate member at a distal end thereof, thereby forming a pair of jaws, said step of opening including the step of separating a pair of parallel arms by shifting said arms perpendicularly away from one another while maintaining each of the arms in an orientation extending parallel to a longitudinal axis of said elongate member; and
moving said jaws towards an internal organ of the patient to insert a portion of said organ between said jaws; and
shifting said arms towards one another to at least partially close said jaws about said organ.

10. The method defined in claim 9, further comprising the step of inflating a balloon element connected to said jaws, thereby forming a cushion for clamping said organ.

11. The method defined in claim 9, further comprising the step of displacing said organ relative to other organic tissues of the patient by exerting a force on said elongate member and said jaws upon completion of said step of shifting.

12. The method defined in claim 9 wherein said balloon element is in a collapsed configuration during said step of inserting.

13. The method defined in claim 9 wherein said balloon element is one of a pair of balloon elements attached to respective ones of said jaws, said step of inflating comprising the step of inflating said balloon elements simultaneously.

14. The method defined in claim 9 wherein said step of inflating is executed subsequently to said step of moving.

15. The method defined in claim 9 wherein said step of inflating is executed prior to said step of moving.

16. The method defined in claim 9 wherein said step of inserting includes the step of inserting said elongate member through a trocar sleeve into the patient's abdomen, said method being part of a laparoscopic procedure.

* * * * *

UNITED STATES PATENT AND TRADEMARK OFFICE
CERTIFICATE OF CORRECTION

PATENT NO. : 5,250,074
DATED : October 5, 1993
INVENTOR(S) : Peter J. Wilk and Jonathan Tiefenbrun It is certified that error appears in the above-identified patent and that said Letters Patent is hereby corrected as shown below:

Column 4, line 25 change "10" (second occurrence) to --IO--.

Column 5, line 23, change "annd" to --and--.

Column 7, line 6, change "claim 1" to --claim 2--.

Column 7, line 9, change "claim 1" to --claim 2--.

Column 8, line 15, change "claim 9" to --claim 10--.

Column 8, line 18, change "claim 9" to --claim 10--.

Column 8, line 23, change "claim 9" to --claim 10--.

Column 8, line 26, change "claim 9" to --claim 10--.

Signed and Sealed this

Nineteenth Day of April, 1994

Attest:

BRUCE LEHMAN

*Attesting Officer*        *Commissioner of Patents and Trademarks*